US009808455B2

(12) United States Patent
Chuang et al.

(10) Patent No.: US 9,808,455 B2
(45) Date of Patent: *Nov. 7, 2017

(54) COMBINATIONS COMPRISING 3-PHENYLSULFONYL-8-PIPERAZINYL-1YL-QUINOLINE

(71) Applicant: Axovant Sciences GmbH, Basel (CH)

(72) Inventors: Tsu Tshen Chuang, Essek (GB); Ann Jacqueline Hunter, Hertfordshire (GB); David John Virley, Essex (GB)

(73) Assignee: Axovant Sciences GmbH, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/802,036

(22) Filed: Jul. 17, 2015

(65) Prior Publication Data
US 2015/0320742 A1    Nov. 12, 2015

Related U.S. Application Data

(63) Continuation of application No. 12/746,968, filed as application No. PCT/EP2008/067225 on Dec. 10, 2008, now Pat. No. 9,084,742.

(30) Foreign Application Priority Data

Dec. 12, 2007 (GB) .................................. 0724281.1
Dec. 12, 2007 (GB) .................................. 0724285.2

(51) Int. Cl.
*A61K 31/496* (2006.01)
*A61K 45/06* (2006.01)
*A61K 31/4523* (2006.01)
*A61K 31/13* (2006.01)
*A61K 31/519* (2006.01)
*A61K 31/4525* (2006.01)
*A61K 31/00* (2006.01)
*A61K 31/5513* (2006.01)

(52) U.S. Cl.
CPC .......... *A61K 31/496* (2013.01); *A61K 31/00* (2013.01); *A61K 31/13* (2013.01); *A61K 31/4525* (2013.01); *A61K 31/519* (2013.01); *A61K 31/5513* (2013.01); *A61K 45/06* (2013.01)

(58) Field of Classification Search
CPC .............. A61K 31/496; A61K 31/4523; A61K 32/5513
See application file for complete search history.

(56) References Cited

U.S. PATENT DOCUMENTS

| 5,576,338 A | 11/1996 | Friesen et al. |
| 5,596,001 A | 1/1997 | Hamanaka |
| 6,172,084 B1 | 1/2001 | Cuny et al. |
| 6,187,805 B1 | 2/2001 | Pineiro et al. |
| 6,207,679 B1 | 3/2001 | Cuny et al. |
| 6,310,212 B1 | 10/2001 | Yuan et al. |
| 6,316,450 B1 | 11/2001 | Bromidge et al. |
| 6,376,670 B1 | 4/2002 | Cuny et al. |
| 6,380,199 B1 | 4/2002 | Reavill et al. |
| 6,403,808 B1 | 6/2002 | Glennon et al. |

(Continued)

FOREIGN PATENT DOCUMENTS

| CA | 2169231 A1 | 8/1996 |
| EP | 0030023 A2 | 6/1981 |

(Continued)

OTHER PUBLICATIONS

"The Merck Manual of Diagnosis and Therapy", Merck Research Laboratories, pp. 1769-1781 (2006).

(Continued)

*Primary Examiner* — Samira Jean-Louis
(74) *Attorney, Agent, or Firm* — Pepper Hamilton LLP

(57) ABSTRACT

The combination of 3-phenylsulfonyl-8-piperazinyl-1yl-quinoline or a pharmaceutically acceptable salt thereof with a second therapeutic agent, wherein the second therapeutic agent is selected from:
(a) a therapeutic agent known to modify cholinergic transmission such as M1 muscarinic receptor agonists or allosteric modulators, M2 muscarinic antagonists, acetylcholinesterase inhibitors, nicotinic receptor agonists or allosteric modulators, 5-HT4 receptor partial agonists or 5HT1A receptor antagonists and NMDA receptor antagonists or modulators, glutamate antagonists, GABA-ergic antagonists, H3 antagonists, putative metabolic/mitochondrial modulators, or disease modifying agents such as β or γ-secretase inhibitors, Tau-targeted therapeutics, β-amyloid aggregation inhibitors and β-amyloid immunotherapies;
(b) an antidepressant such as a tricyclic, a MAOI (Monoamine oxidase inhibitor) a SSRI (Selective Serotonin Reuptake Inhibitor), a SNRI (Serotonin and Noradrenaline Reuptake Inhibitor) or a NaSSA (noradrenergeric and specific serotonergic antidepressant);
(c) an atypical antipsychotic, for example olanzapine, clozapine, prisperidone, quentiapine, aripriprazole or paliperiden; or
(d) a therapeutic agent suitable for use in Attention Deficit Disorders/Hyperactivity Syndrome, e.g. methylphenidate (Ritalin) or dexamfetamine (Dexedrine),
and also the use of 3-phenylsulfonyl-8-piperazinyl-1yl-quinoline or a pharmaceutically acceptable salt thereof for the treatment of:
a) psychiatric disorders with prominent cognitive deficits e.g. chronic PTSD (Post traumatic stress disorder);
b) non-degenerative disorders with prominent cognitive deficits e.g. MS (multiple Sclerosis), post-chemotherapy, post-CABG (Coronary artery bypass graft), post-stroke; and/or
c) paediatric disorders e.g. autism, mental retardation and learning disabilities.

14 Claims, No Drawings

(56) References Cited

U.S. PATENT DOCUMENTS

| | | |
|---|---|---|
| 6,489,488 B2 | 12/2002 | Glennon et al. |
| 6,518,297 B2 | 2/2003 | Glennon et al. |
| 6,548,504 B1 | 4/2003 | Bromidge et al. |
| 6,608,085 B1 | 8/2003 | Gillespie et al. |
| 6,627,661 B2 | 9/2003 | Reavill et al. |
| 6,787,535 B2 | 9/2004 | Beard et al. |
| 6,849,644 B2 | 2/2005 | Bromidge et al. |
| 7,084,169 B2 | 8/2006 | Zhao |
| 7,087,750 B2 | 8/2006 | Caldirola et al. |
| 7,098,233 B2 | 8/2006 | Di Cesare et al. |
| 7,262,188 B2 | 8/2007 | MacDonald et al. |
| 7,452,888 B2 | 11/2008 | Ahmed et al. |
| 7,601,837 B2 | 10/2009 | Ahmed et al. |
| 7,799,774 B2 | 9/2010 | Ahmed et al. |
| 7,943,639 B2 | 5/2011 | Johansson et al. |
| 7,977,337 B2 | 7/2011 | Ahmed et al. |
| 8,236,947 B2 | 8/2012 | Ahmed et al. |
| 8,404,690 B2 | 3/2013 | Page et al. |
| 9,029,379 B2 | 5/2015 | Korenberg et al. |
| 9,084,742 B2 | 7/2015 | Chuang et al. |
| 2001/0051719 A1 | 12/2001 | Bromidge et al. |
| 2002/0115670 A1 | 8/2002 | Kelly et al. |
| 2003/0144505 A1 | 7/2003 | Bromidge et al. |
| 2004/0024210 A1 | 2/2004 | Johansson et al. |
| 2004/0034036 A1 | 2/2004 | Bromidge et al. |
| 2004/0122076 A1 | 6/2004 | Bobb et al. |
| 2004/0132742 A1 | 7/2004 | Bromidge et al. |
| 2004/0167030 A1 | 8/2004 | Bernotas et al. |
| 2005/0090485 A1 | 4/2005 | Bromidge et al. |
| 2005/0090496 A1 | 4/2005 | Ahmed et al. |
| 2005/0124628 A1 | 6/2005 | Ahmend et al. |
| 2005/0176705 A1 | 8/2005 | Bromidge |
| 2005/0176759 A1 | 8/2005 | Ahmed et al. |
| 2006/0035888 A1 | 2/2006 | Jonas et al. |
| 2006/0148818 A1 | 7/2006 | Johansson et al. |
| 2006/0287334 A1 | 12/2006 | Johnson et al. |
| 2007/0027139 A1 | 2/2007 | Johnson et al. |
| 2007/0032504 A1 | 2/2007 | Gladwin |
| 2007/0167431 A1* | 7/2007 | Comery ............... A61K 31/416 514/214.01 |
| 2007/0191345 A1 | 8/2007 | Ahmed et al. |
| 2007/0249603 A1 | 10/2007 | Johnson et al. |
| 2007/0275979 A1 | 11/2007 | MacDonald et al. |
| 2008/0255359 A1 | 10/2008 | Wade |
| 2010/0004264 A1 | 1/2010 | Xiong et al. |
| 2010/0041672 A1 | 2/2010 | Bruton et al. |
| 2010/0226855 A1 | 9/2010 | Nangia et al. |
| 2010/0267691 A1 | 10/2010 | Chuang et al. |
| 2011/0178094 A1 | 7/2011 | Holm et al. |
| 2014/0073681 A1 | 3/2014 | Schmidt et al. |
| 2015/0233698 A1 | 8/2015 | Huang et al. |
| 2016/0324852 A1 | 11/2016 | Friedhoff et al. |

FOREIGN PATENT DOCUMENTS

| | | | | |
|---|---|---|---|---|
| EP | 0605981 B1 | 2/1996 | | |
| EP | 0818449 A1 | 1/1998 | | |
| EP | 0631176 B1 | 12/2000 | | |
| EP | 0867477 B1 | 5/2002 | | |
| EP | 1956004 B1 | 6/2012 | | |
| ES | WO 2007147883 A1 * | 12/2007 | ............ | A61K 31/445 |
| GB | 2341549 A | 3/2000 | | |
| GB | WO 03080580 A2 * | 10/2003 | ............ | C07D 215/00 |
| JP | 02262627 | 10/1990 | | |
| WO | WO 95/11592 A1 | 5/1995 | | |
| WO | WO 97/32858 A1 | 9/1997 | | |
| WO | WO 98/27081 A1 | 6/1998 | | |
| WO | WO 98/47874 A1 | 10/1998 | | |
| WO | WO 98/54157 A1 | 12/1998 | | |
| WO | WO 98/54158 A1 | 12/1998 | | |
| WO | WO 98/57931 A2 | 12/1998 | | |
| WO | WO 98/57952 A1 | 12/1998 | | |
| WO | WO 99/42465 A2 | 8/1999 | | |
| WO | WO 99/47516 A1 | 9/1999 | | |
| WO | WO 99/65906 A1 | 12/1999 | | |
| WO | WO00/12073 A1 | 3/2000 | | |
| WO | WO00/13681 | 3/2000 | | |
| WO | WO00/34265 A2 | 6/2000 | | |
| WO | WO00/42026 A1 | 7/2000 | | |
| WO | WO00/58303 A1 | 10/2000 | | |
| WO | WO00/58313 A1 | 10/2000 | | |
| WO | WO00/63203 A1 | 10/2000 | | |
| WO | WO00/64877 A1 | 11/2000 | | |
| WO | WO01/16108 A2 | 3/2001 | | |
| WO | WO01/17963 A2 | 3/2001 | | |
| WO | WO01/32646 A2 | 5/2001 | | |
| WO | WO01/32660 A1 | 5/2001 | | |
| WO | WO01/40217 A1 | 6/2001 | | |
| WO | WO01/98279 A2 | 12/2001 | | |
| WO | WO02/08178 A1 | 1/2002 | | |
| WO | WO02/20489 A2 | 3/2002 | | |
| WO | WO02/28837 A1 | 4/2002 | | |
| WO | WO02/36562 A2 | 5/2002 | | |
| WO | WO02/44170 A2 | 6/2002 | | |
| WO | WO02/078693 A2 | 10/2002 | | |
| WO | WO02/089811 A1 | 11/2002 | | |
| WO | WO02/098857 A1 | 12/2002 | | |
| WO | WO02/102774 A1 | 12/2002 | | |
| WO | WO03/011284 A1 | 2/2003 | | |
| WO | WO03/013510 A1 | 2/2003 | | |
| WO | WO03/014097 A1 | 2/2003 | | |
| WO | WO03/020707 A1 | 3/2003 | | |
| WO | WO03/035061 A1 | 5/2003 | | |
| WO | WO03/037872 A1 | 5/2003 | | |
| WO | WO03/066056 A1 | 8/2003 | | |
| WO | WO03/072558 A2 | 9/2003 | | |
| WO | WO03/080608 A2 | 10/2003 | | |
| WO | WO03/095434 A1 | 11/2003 | | |
| WO | WO03/104193 A1 | 12/2003 | | |
| WO | WO2004/000828 A1 | 12/2003 | | |
| WO | WO2004/026830 A1 | 4/2004 | | |
| WO | WO2004/026831 A1 | 4/2004 | | |
| WO | WO2004/035047 A1 | 4/2004 | | |
| WO | WO2004/041792 A1 | 5/2004 | | |
| WO | WO2004/050085 A1 | 6/2004 | | |
| WO | WO2004/074243 A2 | 9/2004 | | |
| WO | WO2004/078176 A1 | 9/2004 | | |
| WO | WO2004/080969 A1 | 9/2004 | | |
| WO | WO2005/021530 A1 | 3/2005 | | |
| WO | WO2005/026125 A1 | 3/2005 | | |
| WO | WO2005/030724 A2 | 4/2005 | | |
| WO | WO2005/040124 A1 | 5/2005 | | |
| WO | WO2005/066157 A1 | 7/2005 | | |
| WO | WO2005/095346 A1 | 10/2005 | | |
| WO | WO2005/113539 A1 | 12/2005 | | |
| WO | WO2005/121140 A1 | 12/2005 | | |
| WO | WO2006/038006 A2 | 4/2006 | | |
| WO | WO2006/053785 A1 | 5/2006 | | |
| WO | WO2007/039219 A1 | 4/2007 | | |
| WO | WO2007/039220 A1 | 4/2007 | | |
| WO | WO2007/039238 A1 | 4/2007 | | |
| WO | WO2008/113818 A1 | 9/2008 | | |
| WO | WO2009/074607 A1 | 6/2009 | | |
| WO | 2016179566 A1 | 11/2016 | | |
| WO | 2016179569 A1 | 11/2016 | | |

OTHER PUBLICATIONS

Ahmed et al., "Bicylic heteroarylpiperazines as selective brain penetrant 5-HT6 receptor antagonists," *Bioorganic & Medicinal Chem. Letters*, 15:4867-4871 (2005).

Anonymous, "Drug treats severe Alzheimer's". http://newsvote.bbc.co.uk/mpapps/pagetools/print/news.bbc.co.uk/2/hi/health/4832574.stm. Mar. 23, 2006.

Bentley et al. "5-HT$_6$ Antisense Oligonucleotide I.C.V. Affects Rat Performance in the Water Maze and Feeding" Journal of Psychopharma. (Supplement), A64:255 (1997) Abstract.

Bentley et al., "Effect of the 5-HT6 Antagonist, Ro 04-6790 on Food Consumption in Rats Trained to a Fixed Feeding Regime", British Journal of Pharmacol., 126 (Suppl.): 66 (1999) Abstract.

(56) References Cited

OTHER PUBLICATIONS

Bentley et al., "Investigation of stretching behavior induced by the selective 5-HT6 receptor antagonist, Ro 04-6790, in rats", British Journal of Pharmacol., 126: 1537-1542 (1999).
Birks et al., "Donepezil for dementia due to Alzheimer's disease", The Cochrane Library. http://onlinelibrary.wiley.com/store/10.1002/14651858.CD001190.pub2/asset/CD001190.pdf?v=1&t=h5uxf9xk&s=991bffcda40d23d5edf561ab6543198f531afl6d [retrieved Aug. 14, 2012).
Bos et al., "5-HT6 receptor antagonists" lead optimization and biological evaluation of N-aryl and B-heteroaryl 4-amino-benzene sulfonamides, Eur. J. Med. Chem. 36(2): 165-178 (2001).
Bourson et al., "Determination of the Role of the 5-HT6 Receptor in the Rat Brain: A Study Using Antisense Oligonucelotides", The Journal of Pharmacology & Experimental Therapeutics, 274(1): 173-180 (1995).
Bourson et al., "Involvement of 5-HT6 receptors in nigro-striatal function in rodents," *British J. of Pharmacol.* (1998), 125:1562-1566 (1998).
Branchek et al., "5-HT6 Receptors as Emerging Targets for Drug Discovery," *Annu. Rev. Pharmcol. Toxicol.*, 40: 319-334 (2000).
Bromidge et al., Phenyl Benzenesulfonamides are Novel and Selective 5-HT6 Antagonists: Identification of N-(2,50Dibromo-3-fluorophenyl)-4-methoxy-3-piperazin-1-ylbenzensulfonamide (SB-357134), Bioorganic & Medicinal Chemistry Letters, vol. 11, p. 55-58 (2001).
Callahan et al., "Characterization of the Selective 5-HT6 Receptor Antagonist SB 271046 in Behavioral Models of Cognition", 34th Annual Scientific Meeting of the Soc. for Neurosci., San Diego. Oct. 2004.
Castaneda-Corral et al., "Role of Peripheral and Spinal 5-HT6 Receptors According to the Rat Formalin Test", Neuroscience, 162: 444-452 (2009).
Chang-Fong et al., "1,2,3,4-Tetrahydrocarbazoles as 5-HT6 serotonin receptor ligands," Bioorg. Med. Chem. Lett., 14(8): 1961-1964 (2004).
Chuang et al., "5-HT6 Receptor Antagonist SB-742457 as a Novel Cognitive Enhancing Agent for Alzheimer's Disease", Alzheimer's & Dementia, The Journal of the Alzheimer's Association, 2(3/Supp. 1): S631-S632 (2006).
Clinical Trial Protocol Summaries (Five studies). http://www.gsk-clinicalstudyregister.com/quick-search-list.jsp?item=SB742457&type=Compound&letterrange=Q-U&studyType=All&phase=All&population=All&marketing=All(accessed Mar. 9, 2012).
Davies et al., "Drug discovery targets: 5-HT6 receptor", Drugs of the Future, 30(5): 479-495 (2005).
East et al. "5HT6 receptor binding sites in schizophrenia and following antipsychotic drug administration: Autoradiographic studies with '12515B-258585" Synapse, vol. 45, 2002, pp. 191-199.
European Search Report for EP08157490.7 dated Jul. 8, 2008.
European Search Report for EP12170019.9 dated Aug. 16, 2012.
File "Anxiolytic Action of a Neurokinin, Receptor Antagonist in the Social Interaction Test" Pharmacol. Biochem. Behav. 58(3):747-752 (Nov. 1997) abstract.
File "The Use of Social Interaction as a Method for Detecting Anxiolytic Activity of Chlordiazepoxide-llike Drugs" J. Neuro. Methods, 2(3):219-238 (Jun. 1980) abstract.
Foley et al., "The 5-HT6 Receptor Antagonist SB-271046 Reverses Scopolamine-Disrupted Consolidation of a Passive Avoidance Task and Ameliorates Spatial Task Deficits in Aged Rats", Neuropsychopharmacology, 29: 93-100 (2004).
Garcia-Alloza et al., "Differential Involvement of 5-HT IB/ID and 5-HT6 Receptors in Cognitive and Non-cognitive Symptoms in Alzheimer's Disease", Neuropsychopharmacology, 29: 410-416 (2004).
Gardner "Distress Vocalization in Rat Pups a Simple Screening Method for Anxiolytic Drugs" J. Pharma. Meth. 14(3):181-187 (Nov. 1985) abstract.

Glaxosmithkline Clinical Trial, http://www.gsk-clinicalstudyregister.com/result_comp_list.jsp?compound=SB742457&studyType=All&phase=All&population=All&marketing=All. Sep. 21, 2011.
Glaxosmithkline, A Dose Ranging Study to Investigate the Efficacy and Safety of SB-742457 in Alzheimer's Disease NCT ID No. NCT00224497 (Verified 2007) Clinical Study.
Glaxosmithkline, SB-742457 and Donepezil in Alzheimer's Disease. NCT ID No. NCT00348192 (2006) Clinical Study.
Glennon et al. "2-Substituted Tryptamines: Agents with Selectivity for 5-HT6 Serotonin Receptors" 2000, J. Med. Chem., 43: 1011-1018.
Guy "Clinical Global Impression (CGI)—Severity of Depression Rating Scale" ECDEU Assessment Manual for Psychopharmacology (Rev. Ed. U.S. Dept. of Health, Education and Welvare, Bethesda, MD 1976).
Hamilton "A Rating Scale for Depression" J. Neurol. Neurosurg. Psychiat., 23:56-62 (1960).
Hamilton "Development of a Rating Scale for Primary Depressive Illness" Br. J. Clin. Psych., 6(4):278-296 (Dec. 1967).
Helm et al., "GABAb receptor antagonist SGS742 improves spatial memory and reduces protein binding to the Camp response element (CRE) in the hippocampus", Neuropharmacology, 48:956-964 (2005).
Hirst et al., "Characterization of [25I]-SB-258585 binding to human recombinant and native 5-HT6 receptors in rat, pig and human brain tissue" British Journal of Pharmacology, 2000, 130:1597-1605.
Hirst et al., "Differences in the Central Nervous System Distribution and Pharmacology of the Mouse 5-Hydroxytryptamine-6 Receptor Compared with Rat and Human Receptors Investigated by Radioligand Binding, Site-Directed Mutagenesis, and Molecular Building", Mol. Pharmacol., 64:1295-1308 (2003).
Holenz et al., "Medicinal Chemistry Driven Approaches Toward Novel and Selective Serontonin 5-HT6 Receptor Ligands", J. Med. Chem., 48(6): 1781-1795 (2005).
Ibach et al., "Acetylcholinesterase Inhibition in Alzheimer's Disease", Current Pharmaceutical Design, 10: 231-251 (2004).
International Search Report and Written Opinion for PCT/EP008/067225 dated Mar. 23, 2009.
International Search Report and Written Opinion for PCT/EP2004/010843 dated Mar. 14, 2005.
International Search Report and Written Opinion for PCT/EP2005/012463 dated Feb. 20, 2006.
International Search Report and Written Opinion for PCT/EP2006/009460 dated Dec. 14, 2006.
International Search Report and Written Opinion for PCT/EP2008/053285 dated Jul. 29, 2008.
International Search Report and Written Opinion for PCT/US2016/031359 dated Jul. 29, 2016.
International Search Report for PCT/EP2003/003197 dated Dec. 11, 2003.
Isaac et al. "6-Bicyclopiperazinyl-1-arylsulfonylindoles and 6-Bicyclopiperidinyl-1-arylsulfonylindoles Derivatives as Novel, Potent, and Selective 5-HT6 Receptor Antagonists", Bioorganic & Med. Chem. Letters, 10:1719-1721 (2000).
Johnson et al., "5-HT6 receptor antagonists: Prospects for the treatment of cognitive disorders including dementia", Current Opinion in Drug Discovery and Development, 11(5): 642-654 (2008).
Kan et al., "Association of the HTR6 Polymorphism C267T With Late-Onset Alzheimer's Disease in Chinese", J. Pharmacol. & Exp. Therapeutics, 274: 173-180 (1995).
Khoshkhoo et al., "Crystallization of polymorphs: the effect of solvent", J. Phys. DD: Appl.Phys. 26, pp. B90-B93 (1993).
Liang et al., Olanzapine in the treatment of schizophrenia: a open trial clinical study, Chinese Journal of Psychiatry, 1999, vol. 04, Title pages only.
Lieben et al., "The Selective 5-HT6 Receptor Antagonist Ro4368554 Restores Memory Performance in Cholinergic and Serotonergic Models of Memory Deficiency in the Rat", Neuropsychopharmacology, 30: 2169-2179 (2005).
Lightowler et al. "Anxiolytic-like Effect of Paroxetine in a Rat Social Interaction Test" Pharmacol. Biochem. Behav. 49(2):281-285 (Oct. 1994) (abstract).

(56) References Cited

OTHER PUBLICATIONS

Lindner et al., "An Assessment of the Effects of Serontonin 6 (5-HT6) Receptor Antagonists in Rodent Models of Learning", J. Pharmacol. Exp. Ther., 307(2): 682-691 (2003).
London Stock Exchange Announcement—GlaxoSmithKline (GSK) plc, Issued on Thursday, Dec. 13, 2007, New York, New York.
Maher-Edwards et al, "Double-blind, controlled phase II study of a 5-HT6 receptor antagonist, SB-742457, in Alzheimer's disease", Current Alzheimer Research 7, 374-385 (2010).
Maher-Edwards et al., "SB-742457 and donepezil in Alzheimer disease: a randomized, placebo-controlled study", Int. J. Geriatr. Psychiatry; 26: 536-544 (2011).
Martarello et al.: "Radiolabelling and in vivo evaluation of [11C]GSK215083 as potential PET radioligand for the 5-HT6 receptor in the porcine brain", Journal of Cerebral Blood flow & Metabolism, vol. 25, 2005, p. S598.
Martarello et al.: "Radiolabelling and in vivo evaluation of [11C]GSK215083 as a potential PET radioligand for the 5-HT6 receptor in the porcine brain", J. Label Compd. Radiopharm., vol. 48, 2005, p. S7.
Mitchell et al., "5-HT6 receptors: a novel target for cognitive enhancement", Pharmacol & Therapeutics, 108: 320-333 (2005).
Montgomery et al. "A New Depression Scale Designed to be Sentisive to Change" Br. J. Psychiatry, 134(4):382-389 (Apr. 1979).
Müller, Inorganic Structural Chemistry, Apr. 15, 1993, John Wiley and Sons, 274 pages, pp. 14-15.
Nordberg et al., Cholinesterase Inhibitors in the Treatment of Alzheimer's Disease, Drug Safety, 19(6): 465-480 (1998).
Phase 1 Study, result summary. Study AZ3105822, a single-blind, randomized, placebo-controlled study to evaluate the effect of repeated dosing of an investigational product on the pharmacokinetics and pharmacodynamics of Warfarin in healthy adult subjects. http://www.gsk-clinicalstudyregister.com/result_detail.jsp?protocolId=105822& studyId=BC2066FF-1606-487D-B093-189458FOAE76&compound=SB742457 (undated).
Phase 2, Study 1, result summary. Study AZ3110865, a study comparing SB-74257 or donepezil versus placebo in subjects with mild-to-moderate Alzheimer's disease. http:..www.gsk-clinicalstudyregister.com/result_detail.jsp?protocolId=AZ3110865&studyId=242C4974-9729-4D30-8F91-327CF0631014&compound=SB742457 (undated).
Phase 2, Study 2, result summary. Study AZ3110866, a fixed dose study of SB-742457 versus placebo when added to existing donepezil treatment in subjects with mild-to-moderate Alzheimer's disease. http://www.gsk- clinicalstudyresgister.com/result_detail.jsp?protocolID=AZ3110866&studyId=B8176 D5B-C331-4621-9303-2BBF51E4690B&compound=SB742457 (undated).
Pineiro-Nunez et al., "Discovery and SAR studies of 2,6-difluorobenzenesulfonic acid 1-methyl-3-(methylopiperidin-4-yl)-1H-indol-5-yl ester, a novel and potent 5-HT6 antagonist treatment of cognitive deficit", 299th ACS Natl. Mtg., Mar. 13-17, San Diego, Abst. Medi 282 (2005).
Porsolt et al. "Behavioral despair in mice: a primary screening test for antidepressants" Arch. Int. Pharmac. Ther. 229(2):327-336 (1977) abstract.
Riemer et al., "Influence of the 5-HT6 Receptor on Acetylcholine Release in the Cortex: Pharmacological Characterization of 4-(2-Bromo-6-pyrrolidin-1-ylpyridine-4-sulfonyl)phenylamine, a Potent and Selective 5-HT6 Receptor Antagonist", Brief Articles, J. Med. Chem. 46: 1273-1276 (2003).
Roberts et al., "The distribution of 5-HT6 receptors in rat brain: an autoradiographic binding study using the radiolabeled 5-HT6 receptor antagonist '12515B-258585" Brain Research, vol. 934, 2002, pp. 49-57.
Robichaud et al., "Ch. 2: Recent Advances in Selective Serotonin Receptor Modulation", in Annual Reports in Medicinal Chemistry, vol. 36, p. 11-20 (2000).

Rogers et al., "5-HT6 Receptor Antagonists Enhance Retention of a Water Maze Task in the Rat", Psychopharmacology, 158: 114-119 (2001).
Rojas-Fernandez, "Successful Use of Donepezil for the Treatment of Dementia with Lewy Bodies", Annals of Pharmacotherapy, 35(2): 202-205 (2001).
Roth et al., "Serotonin receptors represent highly favorable molecular targets for cognitive enhancement in schizophrenia and other disorders", Psychopharmacology, 174: 17-24 (2004).
Russell et al., "N-Arylsulfonylindole Derivatives as Serotonin 5-HT6 Receptor Ligands", J. Med. Chem., 44(23): 3881-3895 (2001).
Shua-Haim et al., "Safety, Tolerability, and Caregiver's Impressions of Combination Therapy With Rivastigmine and Memantine for the Treatment of Alzheimer's Disease", Neurobiology & Aging, S205: P1-377(2004).
Sleight et al., "Characterization of Ro 04-6790 and Ro 63-0563: potent and selective antagonists at human and rat 5-HT6 receptors", British Journal of Phamacol., 124: 556-562 (1998).
Stadler et al., "5-HT6 antagonists: a novel approach for the symptomatic treatment of Alzheimer's Disease", 37th IUPAC Cong. Aug. 14-19, Berlin, Abst. MM-7 (1999).
Thome et al., "Association analysis of HTR6 and HTR2A polymorphisms in sporadic Alzheimer's disease", Journal of Neural Transmission, 108: 1175-1180 (2001).
Totterdell, "Synaptic Circutry of Interactions Between Limbic and Dopaminergic Afferents to the Ventral Striatum", International Journal of Neuropsychopharmacology, 7:S14 SP.11.01 (2004).
Tsai et al., "Association Analysis of the 5-HT6 Receptor Polymorphism C267T in Alzheimer's Disease", Neuroscience Letters, 276: 138-139 (1999).
Vasilevskii, "Oxidative Iodination of Substituted N-Methylpyrazoles," Bull. Acad. Sci. USSR (1980), 29(5):778-784.
Vippagunta et al. "Crystalline Solids" (2001) *Advanced Drug Delivery Reviews* 48:3-26.
Willner "Animal Models as Simulations of Depression" Trends Pharmacol. Sci. 12(4):131-136 (1991) abstract.
Woolley et al., "5-HT6 Receptors", Current Drug Targets—CNS & Neurological Disorders, 3: 59-79 (2004).
Woolley et al., "A role for 5-HT6 Receptors in Retention of Spatial Learning in the Morris Water Maze", Neuropharmacology, 41: 210-219 (2001).
Woolley et al., "Reversal of a cholinergic-induced deficit in a rodent model of recognition memory by the selective 5-HT6 receptor antagonist, Ro 04-6790", Psychopharmacology, 170: 358-367 (2003).
International Search Report and Written Opinion for PCT/US2016/031367 dated Aug. 4, 2016.
Pandis et al. "Seizures in Alzheimer Disease: Clinical and Epidemiological Data" (Sep.-Oct. 2012) Epilepsy Currents 12(5):184-187.
International Search Report and Written Opinion for PCT/US2017/019758 dated May 8, 2017.
Mirelman et al. "Virtual Reality for Gait Training: Can It Induce Motor Learning to Enhance Complex Walking and Reduce Fall Risk in Patients With Parkinson's Disease" (Feb. 2011) J. Gerontology: Med. Sci. 66A(2):234-240.
Montero-Odasso et al. "Gait and Cognition: A Complementary Approach to Understanding Brain Function and the Risk of Falling" (Nov. 2012) J. Am. Geriatr. Soc. 60(11):2127-2136.
Montero-Odasso et al. "Can Cognitive Enhancers Reduce the Risk of Falls in Older People with Mild Cognitive Impairment? A Protocol for a Randomised Controlled Double Blind Trial" (Aug. 2, 2009) BMC Neurology 9(42):1-12.
Stebbins et al. "How to Identify Tremor Dominant and Postural Instability/Gait Difficulty Groups with the Movement Disorder Society Unified Parkinson's Disease Rating Scale: Comparison With the Unified Parkinson's DiseaseRating Scale" (2013) Movement Disorders 28(5):668-670.

\* cited by examiner

COMBINATIONS COMPRISING 3-PHENYLSULFONYL-8-PIPERAZINYL-1YL-QUINOLINE

CROSS-REFERENCE TO RELATED APPLICATIONS

This application is a continuation application of U.S. patent application Ser. No. 12/746,968 filed on Jun. 9, 2010 entitled "Combinations Comprising 3-Phenylsulfonyl-8-Piperazinyl-1YL-Quinoline", which is a National Stage filing under 35 U.S.C. §371 of International Patent Application No. PCT/EP2008/067225, filed Dec. 10, 2008 entitled "Combinations Comprising 3-Phenylsulfonyl-8-Piperazinyl-1YL-Quinoline", which claims the priority of United Kingdom Application Nos. 0724281.1 and 0724285.2, both filed on Dec. 12, 2007, the contents which are incorporated herein by reference in their entireties.

The present application relates to new uses of 5-HT$_6$ receptor antagonists, specifically 3-phenylsulfonyl-8-piperazinyl-1yl-quinoline, and to the combination of 5-HT$_6$ receptor antagonists, specifically 3-phenylsulfonyl-8-piperazinyl-1yl-quinoline, with a second therapeutic agent.

WO03/080580 discloses compounds of formula (I) and pharmaceutically acceptable salts thereof:

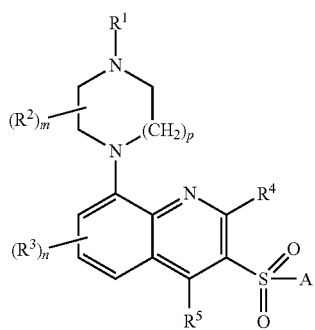

(I)

wherein:

$R^1$ and $R^2$ independently represent hydrogen or $C_{1-6}$ alkyl or $R^1$ is linked to $R^2$ to form a group $(CH_2)_2$, $(CH_2)_3$ or $(CH_2)_4$;

$R^3$, $R^4$ and $R^5$ independently represent hydrogen, halogen, cyano, —$CF_3$, —$CF_3O$, $C_{1-6}$ alkyl, $C_{1-6}$ alkoxy, $C_{1-6}$ alkanoyl or a group —$CONR^6R^7$;

$R^6$ and $R^7$ independently represent hydrogen or $C_{1-6}$ alkyl or together may be fused to form a 5- to 7-membered aromatic or non-aromatic heterocyclic ring optionally interrupted by an O or S atom;

m represents an integer from 1 to 4, such that when m is an integer greater than 1, two $R^2$ groups may instead be linked to form a group $CH_2$, $(CH_2)_2$ or $(CH_2)_3$;

n represents an integer from 1 to 3;

p represents 1 or 2;

A represents a group —$Ar^1$ or —$Ar^2Ar^3$;

$Ar^1$, $Ar^2$ and $Ar^3$ independently represent an aryl group or a heteroaryl group, both of which may be optionally substituted by one or more (e.g. 1, 2 or 3) substituents which may be the same or different, and which are selected from the group consisting of halogen, hydroxy, cyano, nitro, trifluoromethyl, trifluoromethoxy, $C_{1-6}$ alkyl, trifluoromethanesulfonyloxy, pentafluoroethyl, $C_{1-6}$ alkoxy, aryl$C_{1-6}$ alkoxy, $C_{1-6}$ alkylthio, $C_{1-6}$ alkoxy$C_{1-6}$ alkyl, $C_{3-7}$ cycloalkyl$C_{1-6}$ alkoxy, $C_{1-6}$ alkanoyl, $C_{1-6}$ alkoxycarbonyl, $C_{1-6}$ alkylsulfonyl, $C_{1-6}$ alkylsulfinyl, $C_{1-6}$ alkylsulfonyloxy, $C_{1-6}$ alkylsulfonyl$C_{1-6}$ alkyl, arylsulfonyl, arylsulfonyloxy, arylsulfonyl$C_{1-6}$ alkyl, $C_{1-6}$ alkylsulfonamido, $C_{1-6}$ alkylamido, $C_{1-6}$ alkylsulfonamido$C_{1-5}$ alkyl, $C_{1-6}$ alkylamido$C_{1-6}$ alkyl, arylsulfonamido, arylcarboxamido, arylsulfonamido$C_{1-6}$ alkyl, arylcarboxamido$C_{1-6}$ alkyl, aroyl, aroyl$C_{1-6}$ alkyl, aryl$C_{1-6}$ alkanoyl, or a group $CONR^8R^9$ or $SO_2NR^8R^9$, wherein $R^8$ and $R^9$ independently represent hydrogen or $C_{1-6}$ alkyl or together may be fused to form a 5- to 7-membered aromatic or non-aromatic heterocyclic ring optionally interrupted by an C or S atom;

or solvates thereof.

Specifically disclosed is 3-phenylsulfonyl-8-piperazinyl-1yl-quinoline (Example 16) and its hydrochloride salt (Example 2).

3-Phenylsulfonyl-8-piperazinyl-1yl-quinoline can be prepared as described in WO03/080580 or by the further process described in WO07/039238. WO05/040124 discloses a further polymorphic form of 3-phenylsulfonyl-8-piperazinyl-1yl-quinoline as Form III. These International Patent Applications are incorporated herein in their entirety.

Compounds of formula (I) and their pharmaceutically acceptable salts are disclosed in WO03/080580 as having affinity for the 5-HT$_6$ receptor and are believed to be of potential use in the treatment of certain CNS disorders such as anxiety, depression, epilepsy, obsessive compulsive disorders, migraine, cognitive memory disorders (e.g. Alzheimers disease, age related cognitive decline and mild cognitive impairment), Parkinsons Disease, ADHD (Attention Deficit Disorder/Hyperactivity Syndrome), sleep disorders (including disturbances of Circadian rhythm), feeding disorders such as anorexia and bulimia, panic attacks, withdrawal from drug abuse such as cocaine, ethanol, nicotine and benzodiazepines, schizophrenia (in particular cognitive deficits of schizophrenia), stroke and also disorders associated with spinal trauma and/or head injury such as hydrocephalus. WO03/080580 also discloses that Compounds of formula (I) and their pharmaceutically acceptable salts are expected to be of use in the treatment of certain GI (gastrointestinal) disorders such as IBS (Irritable Bowel Syndrome) and in the treatment of obesity.

It will be appreciated by those skilled in the art that the term cognitive memory disorders includes other neurodegenerative disorders associated with dementia, e.g. VaD (Vascular Dementia), DLB (dementia with Lewy Bodies), Mixed AD+CVD (Alzheimer's Disease and Cardiovascular Disease) and HD (Huntingdon's Disease).

US2007/0167431 and WO07/087151 (both Wyeth) disclose a method for the treatment of a cognitive disorder such as Alzheimer's disease in a patient in need thereof which comprises providing to said patient a therapeutically effective amount of a combination of an acetylcholinesterase inhibitor and a 5-HT$_6$ receptor antagonist.

US2007/0167431 discloses that the acetylcholinesterase inhibitors suitable for use are donepezil (i.e. Aricept™ manufactured by Pfizer), galanthamine (i.e. Razadyne™, manufactured by Johnson and Johnson), rivastigmine (i.e. Exelon™, manufactured by Novartis) or any other compounds known to inhibit acetylcholinesterase. A number of patent applications were cited therein which disclosed 5-HT6 antagonists suitable for use. Furthermore the following 5HT6 compounds were listed by name, 3-(1-naphthylsulfonyl)-5-piperazin-1yl-1H-indazole, N,N-dimethyl-3-{3-(1-naphthylsulphonyl)-1H-indazol-5-yl]oxy}propan-1-amine, (2-{[3-(1-naphthylsulphonyl)-1H-indazol-7-yl]oxy}ethyl)amine, 1-(phenylsulphonyl)-4-(1-piperazinyl)-1H-indazole, 5-chloro-N-[4-methoxy-3-(1-piperazinyl)

phenyl]-3-methylbenzo(b)thiophene-2-sulfonamide (SB-271046), 4-amino-N-[2,6-bis(methylamino)pyrimidin-4-yl]benzenesulfonamide (Ro 04-6790, 4-amino-N-[2,6-bis(methylamino)pyridin-4-y]benzenesulfonamide (Ro 63-0563), SB357134, SB399885, GSK-742457, LY4833518/SGS-518, Ro43-68554 and PRX-07034.

The present invention provides the combination of a 5-HT$_6$ receptor antagonist, specifically 3-phenylsulfonyl-8-piperazinyl-1yl-quinoline or a pharmaceutically acceptable salt thereof, with a second therapeutic agent. In one embodiment the present invention provides a combination of 3-phenylsulfonyl-8-piperazinyl-1yl-quinoline or a pharmaceutically acceptable salt thereof with a therapeutic agent known to modify cholinergic transmission such as M1 muscarinic receptor agonists or allosteric modulators, M2 muscarinic antagonists, acetylcholinesterase inhibitors, nicotinic receptor agonists or allosteric modulators, 5-HT4 receptor partial agonists or 5HT1A receptor antagonists and NMDA receptor antagonists or modulators, glutamate antagonists, GABA-ergic antagonists, H3 antagonists, putative metabolic/mitochondrial modulators, or disease modifying agents such as β or γ-secretase inhibitors, Tau-targeted therapeutics, β-amyloid aggregation inhibitors and β-amyloid immunotherapies.

Examples of putative metabolic/mitochondrial modulators are Ketasyn™, RSG-XR, intranasal insulin and Dimebon.

Examples of β-amyloid aggregation inhibitors and β-amyloid immunotherapies include PBT2 (Prana Biotechnology), ELND005/AZD-103 (Elan and Transition Therapeutics), Gammagard/IGIV (Baxter International), monoclonal antibody LY2062430 (Eli Lilly), and bapineuzumab (Wyeth/Elan).

Examples of Tau-targeted therapeutics include tetramethylthionine chloride (REMBER™, TauRX) and AL-108 (Allon).

This combination may be useful in the treatment of cognitive memory disorders, for example Alzheimer's disease, age related cognitive decline and mild cognitive impairment, neurodegenerative disorders for example dementia including vascular dementia (VaD), dementia with Lewy Bodies (DLB), Alzheimer's Disease and Cardiovascular Disease (Mixed AD+CVD) and Huntingdon's Disease (HD).

Accordingly the present invention also provides a method for the treatment of cognitive memory disorders, for example Alzheimer's disease, age related cognitive decline and mild cognitive impairment, neurodegenerative disorders for example dementia including vascular dementia (VaD), dementia with Lewy Bodies (DLB), Alzheimer's Disease and Cardiovascular Disease (Mixed AD+CVD) and Huntingdon's Disease (HD) in a patient in need thereof which comprises providing to said patient a therapeutically effective amount of a combination of 3-phenylsulfonyl-8-piperazinyl-1 yl-quinoline or a pharmaceutically acceptable salt thereof, with a therapeutic agent known to modify cholinergic transmission such as M1 muscarinic receptor agonists or allosteric modulators, M2 muscarinic antagonists, acetylcholinesterase inhibitors, nicotinic receptor agonists or allosteric modulators, 5-HT4 receptor partial agonists or 5HT1A receptor antagonists and NMDA receptor antagonists or modulators, glutamate antagonists, GABA-ergic antagonists, H3 antagonists, putative metabolic/mitochondrial modulators, or disease modifying agents such as β or γ-secretase inhibitors, Tau-targeted therapeutics, β-amyloid aggregation inhibitors and β-amyloid immunotherapies.

One embodiment is directed to combinations of 3-phenylsulfonyl-8-piperazinyl-1yl-quinoline or a pharmaceutically acceptable salt thereof and a second therapeutic agent selected from donepezil, rivastigmine, tetrahydroaminoacridine, memantine, galantamine, 6-[(3-cyclobutyl-2,3,4,5-tetrahydro-1H-3-benzazepin-7-yl)oxy]-N-methyl-3-pyridinecarboxamide hydrochloride or 1-{6-[(3-cyclobutyl-2,3,4,5-tetrahydro-1H-3-benzazepin-7-yl)oxy]-3-pyridinyl}-2-pyrrolidinone.

At a mechanistic level, pharmacodynamic interactions between an acetylcholinesterase inhibitor and a 5HT$_6$ receptor antagonist are feasible. In preclinical studies in rats 3-phenylsulfonyl-8-piperazinyl-1yl-quinoline induces a small increase in the extra cellular levels of acetylcholine in the prefrontal cortex. Although the underlying mechanism is still unknown, it is likely due to increases in the release of acetylcholine from cholinergic neurons, On the other hand, donepezil increases the extracellular levels of acetylcholine by inhibiting the acetylcholinesterase to reduce the degradation of acetylcholine. Therefore this action may prevent the degradation of acetylcholine induced by 3-phenylsulfonyl-8-piperazinyl-1yl-quinoline resulting in a net increased level of acetylcholine that may influence cognitive functions.

In another embodiment the present invention provides a combination of 3-phenylsulfonyl-8-piperazinyl-1yl-quinoline or a pharmaceutically acceptable salt thereof with an antidepressant, for example a tricyclic, a MAOI (Monoamine oxidase inhibitor) a SSRI (Selective Serotonin Reuptake Inhibitor), a SNRI (Serotonin and Noradrenaline Reuptake Inhibitor) or a NaSSA (noradrenergeric and specific serotonergic antidepressant). Examples of specific antidepressant compounds are described below.

| Medication | Trade name | Group |
|---|---|---|
| Amitriptyline | Tryptizol | Tricyclic |
| Clomipramine | Anafranil | Tricyclic |
| Citalopram | Cipramil | SSRI |
| Dosulepin | Prothiaden | Tricyclic |
| Doxepin | Sinequan | Tricyclic |
| Fluoxetine | Prozac | SSRI |
| Imipramine | Tofranil | Tricyclic |
| Lofepramine | Gamanil | Tricyclic |
| Mirtazapine | Zispin | NaSSA |
| Moclobemide | Manerix | MAOI |
| Nortriptyline | Allegron | Tricyclic |
| Paroxetine | Seroxat | SSRI |
| Phenelzine | Nardil | MAOI |
| Reboxetine | Edronax | SNRI |
| Sertraline | Lustral | SSRI |
| Tranylcypromine | Parnate | MAOI |
| Trazodone | Molipaxin | Tricyclic-related |
| Venlafaxine | Efexor | SNRI |

In a further embodiment the present invention provides a combination of 3-phenylsulfonyl-8-piperazinyl-1yl-quinoline or a pharmaceutically acceptable salt thereof and an atypical antipsychotic, for example olanzapine, clozapine, prisperidone, quentiapine, aripriprazole or paliperiden.

This combination may be useful in the treatment of schizophrenia. Accordingly, in yet another aspect the present invention provides a method for the treatment of schizophrenia in a patient in need thereof which comprises providing to said patient a therapeutically effective amount of a combination of 3-phenylsulfonyl-8-piperazinyl-1yl-quinoline or a pharmaceutically acceptable salt thereof, with an atypical antipsychotic, for example olanzapine, clozapine, prisperidone, quentiapine, aripriprazole or paliperiden.

In a further embodiment the present invention provides a combination of 3-phenylsulfonyl-8-piperazinyl-1yl-quinoline or a pharmaceutically acceptable salt thereof and a second therapeutic agent suitable for use in Attention Deficit Disorders/Hyperactivity Syndrome, e.g. methylphenidate (Ritalin) or dexamfetamine (Dexedrine).

In a further aspect the present invention also provides the use of a combination of 3-phenylsulfonyl-8-piperazinyl-1yl-quinoline or a pharmaceutically acceptable salt thereof and a second therapeutic agent in the manufacture of a medicament for use in the treatment of the above disorders.

Accordingly, in one embodiment the present invention provides the use of a combination of 3-phenylsulfonyl-8-piperazinyl-1yl-quinoline or a pharmaceutically acceptable salt thereof with a therapeutic agent known to modify cholinergic transmission such as M1 muscarinic receptor agonists or allosteric modulators, M2 muscarinic antagonists, acetylcholinesterase inhibitors, nicotinic receptor agonists or allosteric modulators, 5-HT4 receptor partial agonists or 5HT1A receptor antagonists and NMDA receptor antagonists or modulators, glutamate antagonists, GABAergic antagonists, H3 antagonists, putative metabolic/mitochondrial modulators, or disease modifying agents such as β or γ-secretase inhibitors, Tau-targeted therapeutics, β-amyloid aggregation inhibitors and β-amyloid immunotherapies, in the manufacture of a medicament for use in the treatment of cognitive memory disorders, for example Alzheimer's disease, age related cognitive decline and mild cognitive impairment, neurodegenerative disorders for example dementia including vascular dementia (VaD), dementia with Lewy Bodies (DLB), Alzheimer's Disease and Cardiovascular Disease (Mixed AD+CVD) and Huntingdon's Disease (HD).

In another embodiment the present invention provides the use of a combination of 3-phenylsulfonyl-8-piperazinyl-1yl-quinoline or a pharmaceutically acceptable salt thereof and an atypical antipsychotic, for example olanzapine, clozapine, prisperidone, quentiapine, aripriprazole or paliperiden in the manufacture of a medicament for use in the treatment of schizophrenia.

The present invention is also directed to new uses of 3-phenylsulfonyl-8-piperazinyl-1yl-quinoline or a pharmaceutically acceptable salt thereof; specifically
  a) further psychiatric disorders with prominent cognitive deficits e.g. chronic PTSD (Post traumatic stress disorder);
  b) non-degenerative disorders with prominent cognitive deficits: MS (multiple Sclerosis), post-chemotherapy, post-CABG (Coronary artery bypass graft), post-stroke; and
  c) paediatric disorders: autism, mental retardation and learning disabilities.

The invention further provides a method of treatment or prophylaxis of these disorders, in mammals including humans, which comprises administering to the sufferer a therapeutically effective amount of 3-phenylsulfonyl-8-piperazinyl-1yl-quinoline or a pharmaceutically acceptable salt thereof.

The invention also provides the use of a 3-phenylsulfonyl-8-piperazinyl-1yl-quinoline or a pharmaceutically acceptable salt thereof in the manufacture of a medicament for use in the treatment or prophylaxis of these disorders.

The invention also provides combinations of 3-phenylsulfonyl-8-piperazinyl-1yl-quinoline and a second therapeutic agent for use in these disorders.

In respect of the treatment of PTSD, the second therapeutic agent may be selected from: serotonergic antidepressants (SSRIs), e.g. fluoxetine (Prozac), sertraline (Zoloft), paroxetine (Paxil), trazodone (Desyrel); medicines that help decrease the physical symptoms associated with PTSD, e.g. clonidine (Catapres), guaneficine (Tenex), and propranolol; mood stabilizers such as lamotrigine (Lamictal), tiagabine (Gabitril), divalproex sodium (Depakote); monoamine oxadazine inhibitors, phenelzine (Nardil); antiadrenergic agents, e.g. clonidine (Catapres), propanolol (Inderal) and guanfacine (Tenex), mood stabilizers that are also antipsychotics, like risperidone (Risperdal), olanzapine (Zyprexa), and quetiapine (Seroquel).

In respect of the treatment of MS, the second therapeutic agent may be selected from: steroids, e.g. methylprednisolone (e.g. Depo-Medrone), prednisone, dexamethasone disease-modifying agents e.g. interferon beta-la (Avonex or Rebif), interferon beta-1b (Betaferon), glatiramer acetate (Copaxone) injections or mitoxantrone (Novantrone); symptomatic agents e.g. Muscle Relaxants (Baclofen, Dantrolene, Tizanidine, Cyclobenzaprine, Clonazepam, Diazepam); Anticholinergics (Propantheline, Tolterodine Dicyclomine); Urinary Tract Antispasmodics (Oxybutynin); Tricyclic Antidepressants (Amitriptyline, Imipramine); Antidiuretic Hormone (desmopressin and desmopressin acetate); Anticonvulsants (carbamazepine, phenytoin, acetazolamide, lamotrigine); Central Nervous System Stimulants (pemoline); Selective Serotonin Reuptake Inhibitors (SSRIs) (citalopram, fluoxetine, paroxetine, sertraline); Non-Steroidal Anti-Inflammatory Drugs (NSAIDS) (ibuprofen, naproxen, ketoprofen); and Phosphodiesterase-5 Inhibitors (sildenafil, tadalafil, vardenafil).

Additionally the second therapeutic agent for use in the treatment of MS or its associated symptoms may be selected from an H3 receptor antagonist, 6-[(3-cyclobutyl-2,3,4,5-tetrahydro-1H-3-benzazepin-7-yl)oxy]-N-methyl-3-pyridinecarboxamide hydrochloride or 1-{6-[(3-cyclobutyl-2,3,4,5-tetrahydro-1H-3-benzazepin-7-yl)oxy]-3-pyridinyl}-2-pyrrolidinone; S1P1 agonists; anti-CD20 monoclonal antibody therapies such as rituximab, ofatumumab; anti-CD3 monoclonal antibody therapies such as otelixizumab; rosiglitazone (Avandia™), alpha 4 integrin antagonist e.g. firategrast, natalizumab (TYSABRI™).

Additionally the second therapeutic agent for use in the treatment of MS or its associated symptoms may be selected from BG12 (Biogen Idec), an S1P agonist e.g. Fingolimod, an immunosuppressant e.g. Laquinimod, Teriflunomide; an estrogen agonist e.g. Trimesta.

In respect of the treatment post chemotherapy, the second therapeutic agent may be selected from: Aldesleukin or IL-2 (Proleukin), Alemtuzumab (MabCampath), Amsacrine (acridinyl anisidide; m-AMSA), Anastrozole (Arimidex), Asparaginase (Crisantaspase), Bevacizumab (Avastin), Bicalutamide (Casodex), Bleomycin, Bortezomib (Velcade), Busulfan, (Campto) Irinotecan, Capecitabine (Xeloda) Carboplatin (Paraplatin), Carmustine (BCNU), Cetuximab, Chlorambucil, Cisplatin, Cladribine (2-CdA, Leustatin), Co-codamol, Cyclophosphamide, Cyproterone acetate (Cyprostat), Cytarabine (Ara C, cytosine arabinoside), Dacarbazine (DTIC), Dactinomycin (Actinomycin D), Daunorubicin, Disodium pamidronate (Aredia), Docetaxel (Taxotere), Doxorubicin, Epirubicin, Erlotinib (Tarceva), Estramustine (Emcyt, Estracyte), Etoposide (VP16, Etopophos), Exemestane (Aromasin), Fentanyl (Durogesic), Fludarabine, Fluorouracil (5FU), Flutamide (Drogenil), Gemcitabine (Gemzar), (Herceptin) Trastuzumab, Goserelin (Zoladex) for breast cancer, Goserelin (Zoladex) for prostate cancer, Hydroxycarbamide (used to be called hydroxyurea), Ibandronic acid (Bondronat), Ibritumomab (Zevalin), Ibuprofen, Idarubicin (Zavedos) Ifosfamide, Imatinib (Glivec), Interferon (Roferon, Intron A), Irinotecan (Campto), Interleukin, lapatinib (Tykerb), Letrozole (Femara), Liposomal Doxorubicin (Caelyx, Myocet, Doxcil), Lomustine (CCNU), Melphalan, Mercaptopurine (6-MP, Purinethol), Methotrexate, Mitomycin C, Mitoxantrone, Morphine, Oxaliplatin, Paclitaxel (Taxol), Pentostatin, Procarbazine, Raltitrexed (Tomudex), Rituximab (Mabthera), Sodium clodronate (Bonefos, Loron), Streptozocin (Zanosar), Steroids, Tamoxifen, (Taxol) Paclitaxel, (Taxotere) Docetaxel, Tegafur with uracil (Uftoral), Temozolomide (Temodal), Tioguanine (Lanvis, 6-TG, 6-tioguanine, Tabloid), Thiotepa (Thioplex, Triethylenethiophosphoramide), (Tomudex) Raltitrexed, Topotecan (Hycamtin), Tretinoin (Vesanoid, ATRA), Treosulfan, Vinblastine (Velban), Vincristine (Oncovin) Vindesine (Eldisine), Vinorelbine (Navelbine), Zevalin (90Y Ibritumomab tiuxetan) and Zoledronic acid (Zometa).

Specifically the second therapeutic agent may be lapatinib, which may also be used in conjunction with capecitabine.

In respect of treatment after a stroke, the second therapeutic agent may be selected from alteplase (Actilyse), aspirin, dipyridamole, fluvastatin sodium (Lescol), clopidogrel hydrogen sulphate (Plavix), ramipril (Tritace) and simvastatin (Simvador, Zocor).

It will be appreciated that reference to treatment is intended to include prophylaxis as well as the alleviation of established symptoms.

The two therapeutic agents may be administered simultaneously or sequentially and, when administration is sequential, either may be administered first. When administration is simultaneous, the combination may be administered either in the same or different pharmaceutical composition.

The two therapeutic agents may be used either as separate formulations or as a single combined formulation. When combined in the same formulation it will be appreciated that the two compounds must be stable and compatible with each other and the other components of the formulation.

Therefore, in further aspect the present invention also provides pharmaceutical compositions comprising an effective amount of a combination of a 5-HT$_6$ receptor antagonist, specifically 3-phenylsulfonyl-8-piperazinyl-1yl-quinoline or a pharmaceutically acceptable salt thereof and a second therapeutic agent, and a pharmaceutically acceptable carrier.

In one embodiment the second therapeutic agent is an agent known to modify cholinergic transmission such as M1 muscarinic receptor agonists or allosteric modulators, M2 muscarinic antagonists, acetylcholinesterase inhibitors, nicotinic receptor agonists or allosteric modulators, 5-HT4 receptor partial agonists or 5HT1A receptor antagonists and NMDA receptor antagonists or modulators, glutamate antagonists GABA-ergic antagonists, H3 antagonists or disease modifying agents such as β or γ-secretase inhibitors.

In another embodiment the second therapeutic agent is an antidepressant, for example a tricyclic, a MAOI (Monoamine oxidase inhibitor) a SSRI (Selective Serotonin Reuptake Inhibitor), a SNRI (Serotonin and Noradrenaline Reuptake Inhibitor) or a NaSSA (noradrenergeric and specific serotonergic antidepressant).

In another embodiment the second therapeutic agent is an atypical antipsychotic, for example olanzapine, clozapine, prisperidone, quentiapine, aripriprazole or palipiriden.

In another embodiment the second therapeutic agent is a therapeutic agent suitable for use in Attention Deficit Disorders/Hyperactivity Syndrome, e.g. methylphenidate (Ritalin) or dexamfetamine (Dexedrine).

When formulated separately they may be provided in any convenient formulation, conveniently in such manner as are known for such compounds in the art.

A pharmaceutical composition may be prepared by admixture, suitably at ambient temperature and atmospheric pressure, and is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

Compositions may, if desired, be presented in a pack or dispenser device which may contain one or more unit dosage forms containing the active ingredients. The pack may, for example, comprise metal or plastic foil, such as a blister pack. Where the compounds are intended for administration as two separate compositions these may be presented, for example, in the form of a twin pack.

Pharmaceutical compositions may also be prescribed to the patient in "patient packs" containing the whole course of treatment in a single package, usually a blister pack. Patient packs have an advantage over traditional prescriptions, where a pharmacists divides a patients supply of a pharmaceutical from a bulk supply, in that the patient always has access to the package insert contained in the patient pack, normally missing in traditional prescriptions. The inclusion of a package insert has been shown to improve patient compliance with the physicians instructions.

It will be understood that the administration of the combination by means of a single patient pack, or patient packs of each composition, including a package insert directing the patient to the correct use of the combination is a desirable additional embodiment.

According to a further embodiment there is provided a patient pack comprising at least one active ingredient, of the combination and an information insert containing directions on the use of the combination.

According to another embodiment there is provided a double pack comprising in association for separate administration of 3-phenylsulfonyl-8-piperazinyl-1yl-quinoline and the second therapeutic agent.

The dose of 3-phenylsulfonyl-8-piperazinyl-1yl-quinoline used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 200 mg, for example 20 to 40 mg; and such unit doses will preferably be administered once a day, although administration more than once a day may be required; and such therapy may extend for a number of weeks or months.

The dose of 3-phenylsulfonyl-8-piperazinyl-1yl-quinoline used in combination with a second therapeutic agent may be same as when it is used on its own or may be different. It may be possible that the dose of either drug used may be lower when used in combination than when used separately.

Suitable behavioural models of cognition known to the person of ordinary skill in the art, for example object recognition memory in young Sprague-Dawley and aged Fisher rats, Water Maze model to investigate spatial learning and memory in young and aged Fisher rats.

A suitable animal model for studying therapeutic drugs against post-traumatic stress disorder is described by Aharon Levy, in Military Medicine, December 2001.

A suitable animal model for studying multiple sclerosis is the experimental autoimmunal encephalomyelitis (EAE) model.

Patient Study for Schizophrenia

The study may be performed as a multicenter, double-blind, placebo controlled randomised, parallel group determination of efficacy of 3-phenylsulfonyl-8-piperazinyl-1yl-quinoline in combination with an atypical antipsychotic agent approved for the treatment of schizophrenia vs an atypical antipsychotic agent approved for the treatment of schizophrenia with placebo.

For example, the study may be performed using a therapeutic dose within the prescribed guidelines of Risperidone.

The patients may receive an appropriate dose of the atypical antipsychotic agent (defined antipsychotic agent or antipsychotic), and, depending on which group they belonged, a therapeutically effective amount 3-phenylsulfonyl-8-piperazinyl-1yl-quinoline once daily or placebo over 12 weeks after a brief wash-out period of earlier antipsychotic medication.

During the wash-out period, a benzodiazepine preparation (mostly lorazepam) may be prescribed, if necessary. Patients with agitation, anxiety, or sleeping problems may be also medicated with lorazepam during the study.

Efficacy and tolerability of 3-phenylsulfonyl-8-piperazinyl-1yl-quinoline/antipsychotic agent vs placebo/antipsychotic agent will be assessed using the following endpoints—positive and negative syndrome scale (PANSS), Clinical Global Impression score (CGI), AIMS, Simpson and Angus, Barnes Akathisia, Calgary Depression Scale and cognition endpoints.

The use of biperiden may be monitored as a possible indicator for side effects of the antipsychotic medication.

In order to exclude the chance that possible differences in the therapeutic effectiveness between the two groups might be due to non-compliance during the antipsychotic therapy or to differences in the antipsychotic agent metabolism, the plasma levels of this drug may be monitored during the study.

The statistics may be performed according to the criterion of "last observation carried forward" (LOCF), i.e., the last PANSS scores of the patients who dropped out before the end of the study were carried forward to all subsequent observation days.

For the comparison of the main efficacy parameter, the mean change in the PANSS between the two treatment groups, t-tests for independent samples may be employed. With reference to the underlying hypothesis of a better outcome of 3-phenylsulfonyl-8-piperazinyl-1yl-quinoline/antipsychotic agent group, a significance of $p<0.05$ may be calculated in the one-tailed t-test and used as the basis for the estimation of the sample size (statistical power) and for the comparison of the groups. For all other comparisons, two-tailed t-tests may be used.

The improved effectiveness of the combination therapy with 3-phenylsulfonyl-8-piperazinyl-1yl-quinoline/antipsychotic agent in comparison to antipsychotic monotherapy may be clearly shown by the significantly lower PANSS global scores after the $2^{nd}$ to 12 weeks of treatment.

Therefore, it could be excluded that the observed differences in the therapeutic effectiveness between the two groups may be due to incompatibility during the antipsychotic agent therapy or differences in antipsychotic metabolism.

The combination of 3-phenylsulfonyl-8-piperazinyl-1yl-quinoline and an atypical antipsychotic agent according to the present invention thus may show improved results compared to the monopreparation of the atypical antipsychotic agent with regard to effectiveness in the treatment of schizophrenia.

Depression/Anxiety Study

Activity of 3-phenylsulfonyl-8-piperazinyl-1yl-quinoline in combination with SSRI inhibitors, vs. depression/anxiety may be evaluated according to the following models:

Porsolt test in mouse for SSRI/TCA (tricyclic antidepressants) (Porsolt et al 1977, Arch Int Pharmacodyn Ther: 229, 327-336);

Chronic mild stress in rat for SSRI/TCA (Willner, 1991, TiPS: 12, 131-136);

Maternal deprivation in rat pups for SSRI (or modulator of serotonin receptors)/TCA (Gardner, 1985, J. Pharmacol. Methods 14: 181-187);

Rat social interaction after chronic treatment with SSRI/TCA (File, 1980 J. Neurosci Methods, 2:219-238; Lightowler et al., 1994, Pharmacol., Biochem. Behaviour: 49, 281-285);

Gerbil social interaction after chronic treatment with SSRI (or modulator of serotonin receptors)/TCA (File, 1997, Pharmacol. Biochem. Behav. 58: 747-752).

Clinical Trials

The usefulness of the compound for treating a Depressive Disorder can be supported by the following studies as described.

Clinical Observations

A double-blind multicenter clinical trial may be designed to assess the safety and efficacy of 3-phenylsulfonyl-8-piperazinyl-1yl-quinoline of the present invention in combination with an SSRI such as paroxetine for treatment of Bipolar Disorder, Bipolar Depression or Unipolar Depression. Patients are randomized to 3-phenylsulfonyl-8-piperazinyl-1yl-quinoline, an SSRI such as paroxetine or 3-phenylsulfonyl-8-piperazinyl-1yl-quinoline plus an SSRI.

In one such study, an 8-week, double blind trial, 28 patients diagnosed with treatment-resistant major depression would be randomized to one of three treatment arms: (1) paroxetine and placebo; (2) 3-phenylsulfonyl-8-piperazinyl-1yl-quinoline and placebo; or (3) paroxetine plus 3-phenylsulfonyl-8-piperazinyl-1yl-quinoline. The efficacy of the treatment may be monitored using the HAMD-21 (Hamilton M. *Journal of Neurology, Neurosurgery & Psychiatry*, 1960.23: 56-62, and Hamilton M. *Development of a rating scale for primary depressive illness*. British Journal of Social and Clinical Psychology. 1967; 6:278-296), Montgomery-Asberg Depression Rating Scale (MADRS) (Montgomery S A, Asberg M. *A new depression scale designed to be sensitive to change*. British Journal of Psychiatry. 1979; 134:382-389), and the Clinical Global Impression (CGI)—Severity of Depression rating scale (Guy, W. ECDEU Assessment Manual for Psychopharmacology. Revised ed. US Dept of Health, Education and Welfare, Bethesda, Md. 1976).

All publications, including but not limited to patents and patent applications, cited in this specification are herein incorporated by reference as if each individual publication were specifically and individually indicated to be incorporated by reference herein as though fully set forth.

The invention claimed is:

1. A method of treating a cognitive memory disorder in a patient in need thereof comprising administering to said patient 20 to 40 mg of 3-phenylsulfonyl-8-piperazinyl-1-yl-quinoline or a pharmaceutically acceptable salt thereof, and a therapeutically effective amount of an acetylcholinesterase inhibitor;
   wherein said cognitive memory disorder is selected from the group consisting of Alzheimer's disease, age related cognitive decline, mild cognitive impairment, and dementia associated with mixed Alzheimer's disease and cardiovascular disease.

2. The method of claim 1, wherein the cognitive memory disorder is Alzheimer's disease.

3. The method of claim 2, wherein the acetylcholinesterase inhibitor is selected from donepezil, galanthamine, rivastigmine, and any combination thereof.

4. The method of claim 1, wherein the dose of 3-phenylsulfonyl-8-piperazinyl-1-yl-quinoline or a pharmaceutically acceptable salt thereof, is administered once a day.

5. The method of claim 1, wherein the dose of 3-phenylsulfonyl-8-piperazinyl-1-yl-quinoline or a pharmaceutically acceptable salt thereof, is administered more than once a day.

6. A method for improving the cognitive function of a patient suffering from Alzheimer's disease, age related cognitive decline, mild cognitive impairment, and dementia associated with mixed Alzheimer's disease and cardiovascular disease comprising administering to said patient 20 to 40 mg of 3-phenylsulfonyl-8-piperazinyl-1-yl-quinoline or a pharmaceutically acceptable salt thereof, and a therapeutically effective amount of an acetylcholinesterase inhibitor.

7. The method of claim 6, wherein the acetylcholinesterase inhibitor is selected from donepezil, galanthamine, rivastigmine, and any combination thereof.

8. A method for the treatment of a cognitive memory disorder in a patient in need thereof comprising administering to said patient a pharmaceutical composition comprising 20 to 40 mg of 3-phenylsulfonyl-8-piperazinyl-1-yl-quinoline or a pharmaceutically acceptable salt thereof, a therapeutically effective amount of an acetylcholinesterase inhibitor, and a pharmaceutically acceptable carrier;
   wherein said cognitive memory disorder is selected from the group consisting of Alzheimer's disease, age related cognitive decline, mild cognitive impairment, and dementia associated with mixed Alzheimer's disease and cardiovascular disease.

9. The method of claim 8, wherein the cognitive memory disorder is Alzheimer's disease.

10. The method of claim 8, wherein the acetylcholinesterase inhibitor is selected from donepezil, galanthamine, rivastigmine, and any combination thereof.

11. The method of claim 8, wherein the therapeutically effective amount of 3-phenylsulfonyl-8-piperazinyl-1yl-quinoline, or a pharmaceutically acceptable salt thereof, is 20 to 40 mg.

12. A method for improving the cognitive function of a patient suffering from Alzheimer's disease, age related cognitive decline, mild cognitive impairment, and dementia associated with mixed Alzheimer's disease and cardiovascular disease comprising administering to said patient a pharmaceutical composition comprising 20 to 40 mg of 3-phenylsulfonyl-8-piperazinyl-1-yl-quinoline or a pharmaceutically acceptable salt thereof, a therapeutically effective amount of an acetylcholinesterase inhibitor; and a pharmaceutically acceptable carrier.

13. The method of claim 12, wherein the acetylcholinesterase inhibitor is selected from donepezil, galanthamine, rivastigmine, and any combination thereof.

14. The method of claim 12, wherein the therapeutically effective amount of 3-phenylsulfonyl-8-piperazinyl-1yl-quinoline, or a pharmaceutically acceptable salt thereof, is 20 to 40 mg.

* * * * *